(12) United States Patent
Mürner

(10) Patent No.: US 7,704,257 B2
(45) Date of Patent: Apr. 27, 2010

(54) COMPRESSION INSTRUMENT

(75) Inventor: Beat Mürner, Reichenbach (CH)

(73) Assignee: Stryker Trauma S.A. (CH)

(*) Notice: Subject to any disclaimer, the term of this patent is extended or adjusted under 35 U.S.C. 154(b) by 437 days.

(21) Appl. No.: 11/285,808

(22) Filed: Nov. 23, 2005

(65) Prior Publication Data

US 2007/0118146 A1    May 24, 2007

(51) Int. Cl.
*A61B 17/58* (2006.01)
(52) U.S. Cl. .................. 606/105; 606/280; 606/86 R
(58) Field of Classification Search .............. 606/86, 606/90, 105, 54, 55, 56, 57, 58, 59, 86 A, 606/86 B, 86 R, 914, 915, 916, 96, 99, 100, 606/280–299, 70, 71; 81/450, 451, 452, 81/453, 454, 455
See application file for complete search history.

(56) References Cited

U.S. PATENT DOCUMENTS

| | | | | |
|---|---|---|---|---|
| 1,395,587 A | * | 11/1921 | McLachlan ................ 29/263 |
| 1,997,466 A | * | 4/1935 | Longfellow ............... 606/59 |
| 2,224,480 A | * | 12/1940 | Kartarik .................... 408/81 |
| 2,301,500 A | * | 11/1942 | Anderson |
| 3,244,170 A | * | 4/1966 | McElvenny |
| 3,386,437 A | * | 6/1968 | Treace |
| 3,534,731 A | * | 10/1970 | Muller |
| 3,540,322 A | * | 11/1970 | Swanson ................... 408/112 |
| 3,709,219 A | * | 1/1973 | Halloran |
| 3,866,607 A | * | 2/1975 | Forsythe et al. ........... 606/105 |
| RE28,841 E | * | 6/1976 | Allgower et al. |
| 4,119,092 A | * | 10/1978 | Gil |
| 4,388,921 A | * | 6/1983 | Sutter et al. |
| RE31,628 E | * | 7/1984 | Allgower et al. |
| 4,502,160 A | * | 3/1985 | Moore et al. ............. 623/23.45 |
| 4,988,349 A | * | 1/1991 | Pennig ...................... 606/58 |
| 5,021,056 A | * | 6/1991 | Hofmann et al. .......... 606/86 |
| 5,167,665 A | * | 12/1992 | McKinney |
| 5,290,281 A | * | 3/1994 | Tschakaloff |
| 5,380,327 A | * | 1/1995 | Eggers et al. |
| 5,429,641 A | * | 7/1995 | Gotfried ..................... 606/67 |
| 5,439,465 A | * | 8/1995 | Tumibay |
| 5,505,733 A | * | 4/1996 | Justin et al. ................ 606/63 |
| 5,632,747 A | * | 5/1997 | Scarborough et al. ..... 606/79 |
| 5,634,926 A | * | 6/1997 | Jobe |
| 5,676,667 A | * | 10/1997 | Hausman |
| 5,785,713 A | * | 7/1998 | Jobe |
| 5,797,912 A | * | 8/1998 | Runciman et al. |

(Continued)

FOREIGN PATENT DOCUMENTS

CH          373 516         11/1963

(Continued)

*Primary Examiner*—Eduardo C Robert
*Assistant Examiner*—Jan Christopher Merene
(74) *Attorney, Agent, or Firm*—Lerner, David, Littenberg, Krumholz & Mentlik, LLP

(57) ABSTRACT

An instrument for use in moving bone fragments of a bone fracture with respect to one another is disclosed. Preferably, movement of a portion of the instrument causes translational movement of a first bone fragment with respect to a second bone fragment. In certain embodiments, the instrument is used in conjunction with a bone plate and an elongate element, such as a K-wire. Methods for utilizing the instrument and moving bone fragments with respect to each other are also disclosed.

22 Claims, 10 Drawing Sheets

U.S. PATENT DOCUMENTS

| | | | |
|---|---|---|---|
| 5,810,824 A * | 9/1998 | Chan | |
| 5,849,012 A * | 12/1998 | Abboudi | |
| 5,935,130 A * | 8/1999 | Kilpela et al. | |
| 5,951,557 A * | 9/1999 | Luter | |
| 5,964,762 A * | 10/1999 | Biedermann et al. | |
| 5,964,763 A * | 10/1999 | Incavo et al. | |
| 5,976,139 A * | 11/1999 | Bramlet | |
| 6,024,745 A * | 2/2000 | Faccioli et al. | 606/54 |
| 6,273,892 B1 * | 8/2001 | Orbay et al. | |
| 6,322,562 B1 * | 11/2001 | Wolter | |
| 6,500,177 B1 * | 12/2002 | Martinelli et al. | 606/57 |
| 6,595,994 B2 * | 7/2003 | Kilpela et al. | |
| 6,641,583 B2 * | 11/2003 | Shluzas et al. | |
| 6,682,533 B1 * | 1/2004 | Dinsdale et al. | |
| 6,695,846 B2 * | 2/2004 | Richelsoph et al. | |
| 6,709,439 B2 * | 3/2004 | Rogers et al. | 606/100 |
| 6,723,098 B1 * | 4/2004 | Shah | |
| 6,852,113 B2 * | 2/2005 | Nathanson et al. | |
| 7,008,432 B2 * | 3/2006 | Schlapfer et al. | 606/90 |
| 7,207,995 B1 * | 4/2007 | Vandewalle | 606/104 |
| 2003/0114856 A1 * | 6/2003 | Nathanson et al. | |
| 2003/0181912 A1 | 9/2003 | Michelson | |
| 2005/0154392 A1 * | 7/2005 | Medoff et al. | |

FOREIGN PATENT DOCUMENTS

| | | | |
|---|---|---|---|
| FR | 2 210 908 | | 7/1974 |
| FR | 2 824 468 | | 11/2002 |
| SU | 594 973 | | 2/1978 |
| WO | WO 90/07304 | * | 7/1990 |
| WO | WO-01/30249 | | 5/2001 |

* cited by examiner

COMPRESSION INSTRUMENT

BACKGROUND OF THE INVENTION

The present invention relates to the field of bone fracture repair, and more particularly, to a compression instrument for use in conjunction with a bone plate.

For many years, bone plates and other fixation means have been widely utilized by doctors and surgeons for repairing fractures formed in bones. Such fractures typically result in otherwise unitary bone structures being split into two or more fragments, with many of these bone fractures resulting in two separate fragments. Essentially, it has been the general practice to reset the different bone fragments to their original position, place a bone plate across the fragments, and affix the plate to each of the fragments through the use of screws or other fixation means. This allows the different fragments to reattach to one another through recalcification so as to permit the fractured pieces to be reformed into the original bone structure. During this process, the affixed bone plate preferably ensures that the fragments remain in their original position, and provides a certain level of support to the bone structure.

Although the above method of rejoining bone fragments caused by fractures has been widely utilized for many years, with overwhelmingly positive results, it is not free from any and all drawbacks. For example, while a simplified fracture repair method is basically described above, many fractures are far from simple. Often times, fractures of bones, such as long bones, are accompanied by other injuries to the body that make it difficult to reset or compress the different bone fragments to their original position. Thus, doctors or surgeons often struggle with the initial resetting of the different fragments of a fractured bone.

Therefore, there exists a need for a compression instrument for use in conjunction with a bone plate or other such device that aids in the resetting or compressing of fractured bone fragments.

SUMMARY OF THE INVENTION

A first aspect of the present invention is a method of moving a first bone fragment with respect to a second bone fragment. The method according to this aspect may include the steps of placing a bone plate adjacent and across the first and second bone fragments, affixing a first side of the bone plate to the first bone fragment, positioning an instrument in a hole formed in the bone plate and arranging an elongate element through a cannulated opening in said instrument and into the second bone fragment, causing a first portion of the instrument to move in a first direction to move a second portion of the instrument in a second direction which is different than said first direction, the movement of the first portion causing the second bone fragment to move with respect to the first bone fragment, and affixing a second side of the bone plate to the second bone fragment. The method may include utilizing fixation means selected from the group consisting of screws, nails, bolts and staples. It is noted that the elongate element may be selected from the group consisting of K-wires, drills, pins, screws, nails and bolts. The method may be performed to move the first and second bone fragments towards or away from one another. In certain embodiments, the instrument may include a handle, a sledge, a sleeve and a knob. In these embodiments, rotation of the knob may move the sledge and sleeve in a direction perpendicular to a longitudinal axis of the handle.

Another aspect of the present invention is a bone compression/displacement instrument. In certain embodiments, the instrument includes a handle having a longitudinal axis, a sledge inserted into a portion of the handle and a knob connected to the handle, the sledge being movable with respect to the handle. Movement of the knob may cause movement of the sledge with respect to the handle. This movement may be in a direction perpendicular to the longitudinal axis of the handle. The instrument may also include a sleeve inserted through the handle and the sledge. The handle may include a cut out section for receiving the sledge and first and third parts of a channel for receiving the sleeve. In addition, the sledge may include a second part of the channel for receiving the sleeve. The sleeve may be sized to move within the first and third parts of the channel. The sleeve may also be cannulated for receiving an elongate element therethrough. In other embodiments, the knob may be threadably connected to the handle and the instrument may include a nut threadably connected to the knob. The sledge may also include at least one groove for cooperating with at least one protrusion of the handle. Rotation of the knob may cause translation of the sledge in a direction perpendicular to the longitudinal axis of the handle. Finally, the handle may further include a tip for insertion into a hole formed through a bone plate.

Yet another aspect of the present invention is a fracture repair kit. In accordance with certain embodiments of this third aspect, the kit includes at least one bone plate, at least one elongate element and at least one instrument each having a first portion adapted to cooperate with the bone plate, a second portion adapted to move with respect to the first portion, and a third portion adapted to cause movement of the second portion with respect to the first portion. The elongate element may be capable of being arranged with the instrument and movement of the second portion of the instrument may be capable of causing the elongate element to move with respect to the first portion of the instrument.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
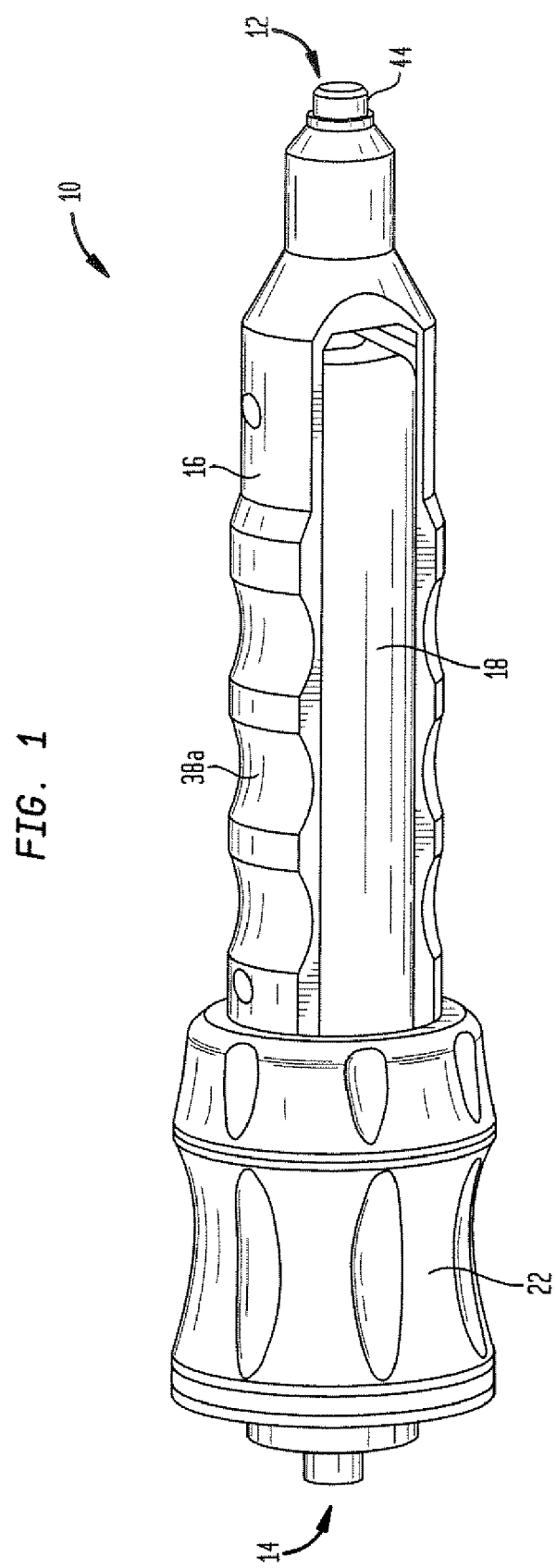
FIG. 1 is a perspective view of a compression instrument in accordance with an embodiment of the present invention.
Figure 2:
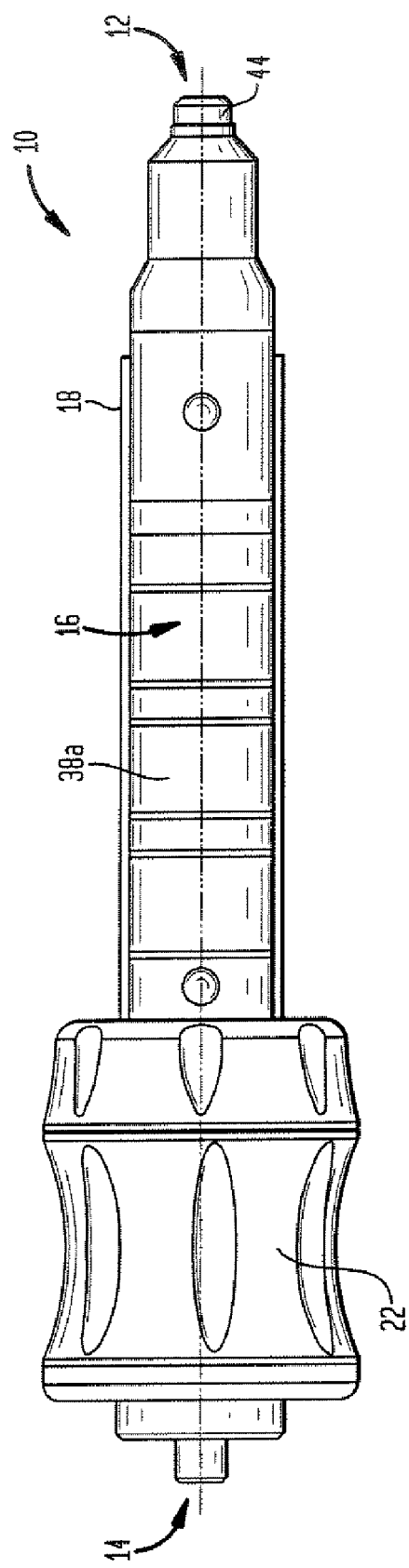
FIG. 2 is a top view of the compression instrument shown in FIG. 1.

Referring to the drawings, wherein like reference numerals refer to like elements, there is shown in FIG. 1, a compression instrument designated generally by reference numeral 10. Compression instrument 10 is preferably usable in conjunction with many different types of bone plates or other such devices, including but not limited to, the bone plate assembly disclosed in commonly owned U.S. patent application Ser. No. 10/999,132 filed on Nov. 29, 2004, the disclosure of which is hereby incorporated by reference herein. However, as would be apparent to those of ordinary skill in the art, compression instrument 10 of the present invention may be easily modified in order to be utilized in conjunction with many different bone plates. This will be discussed further below. As best shown in FIGS. 1 and 2, compression instrument 10 may be an elongate structure having a proximal end 12 and a distal end 14. Compression instrument 10 is preferably sized and configured so as to allow a surgeon or other medical professional to grip and manipulate the instrument. In addition, compression instrument 10 may also be sized so as to allow its insertion into an incision or other opening in the body, as will be more completely discussed below in the discussion relating to the method of utilizing the present invention.

Figure 3:
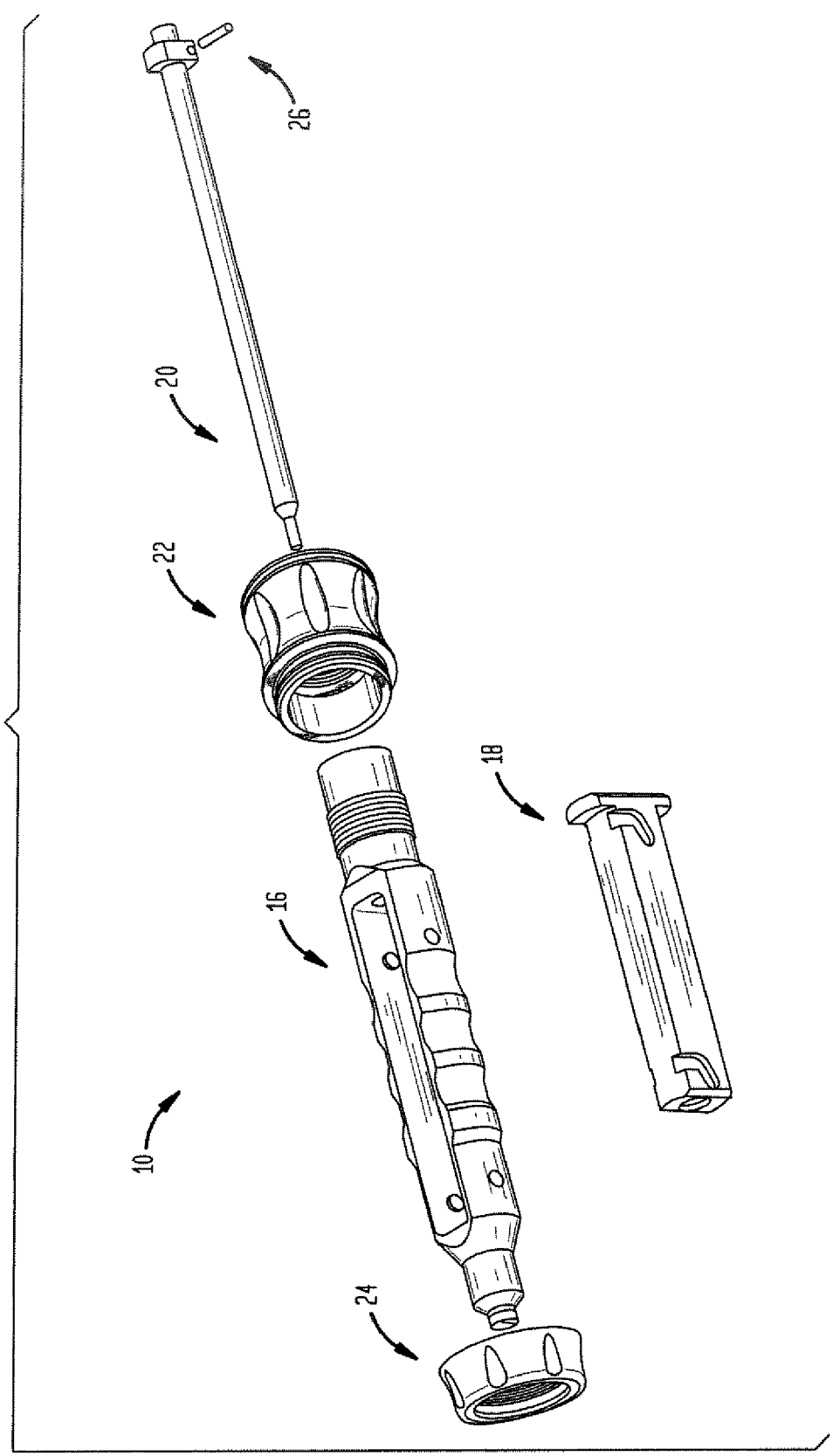
FIG. 3 is an exploded perspective view of the compression instrument shown in FIG. 1.

As best shown in the exploded view of FIG. 3, compression instrument 10 may include a handle 16, a sledge portion 18, a K-wire sleeve 20, a knob 22 and a nut 24. These elements are each more particularly shown in FIGS. 4-8, respectively. Preferably, each of the elements may be interconnected with each other so as to form a single contained unit. However, it is to be understood that compression instrument 10 may include fewer or more elements in its fully constructed form. For example, as shown in FIG. 3, compression instrument 10 may further include a spring assembly 26, which prevents sleeve 20 from falling out of a fully constructed instrument 10. This will be more fully discussed below, as will each of the individual elements of compression instrument 10.

Figure 4:
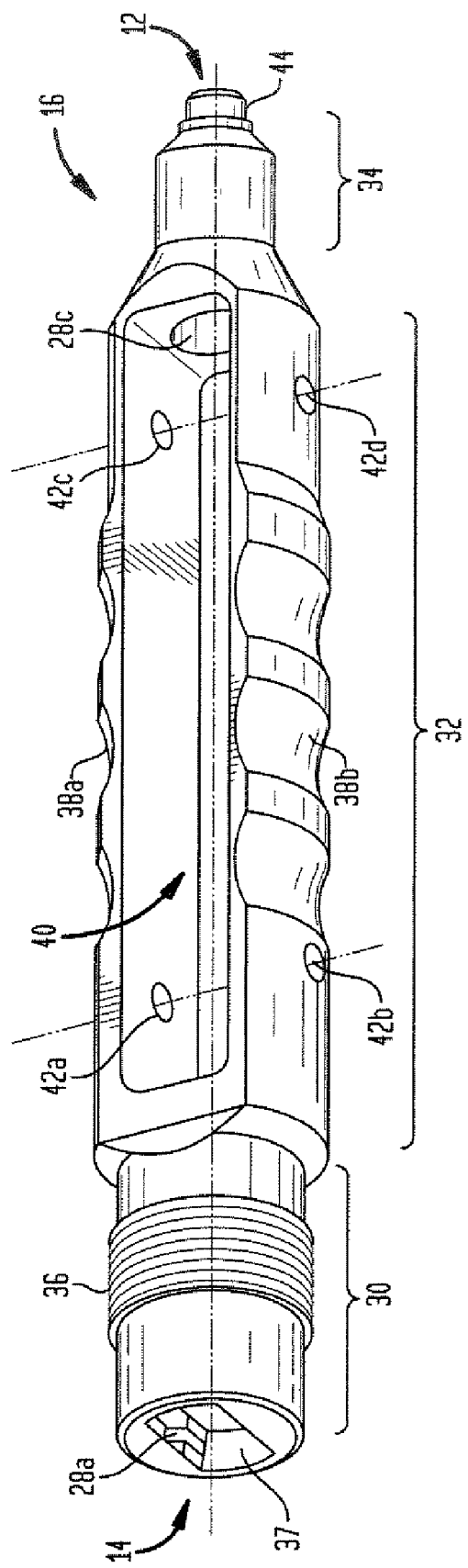
FIG. 4 is a perspective view of a handle portion of the compression instrument shown in FIG. 1.
Figure 9:
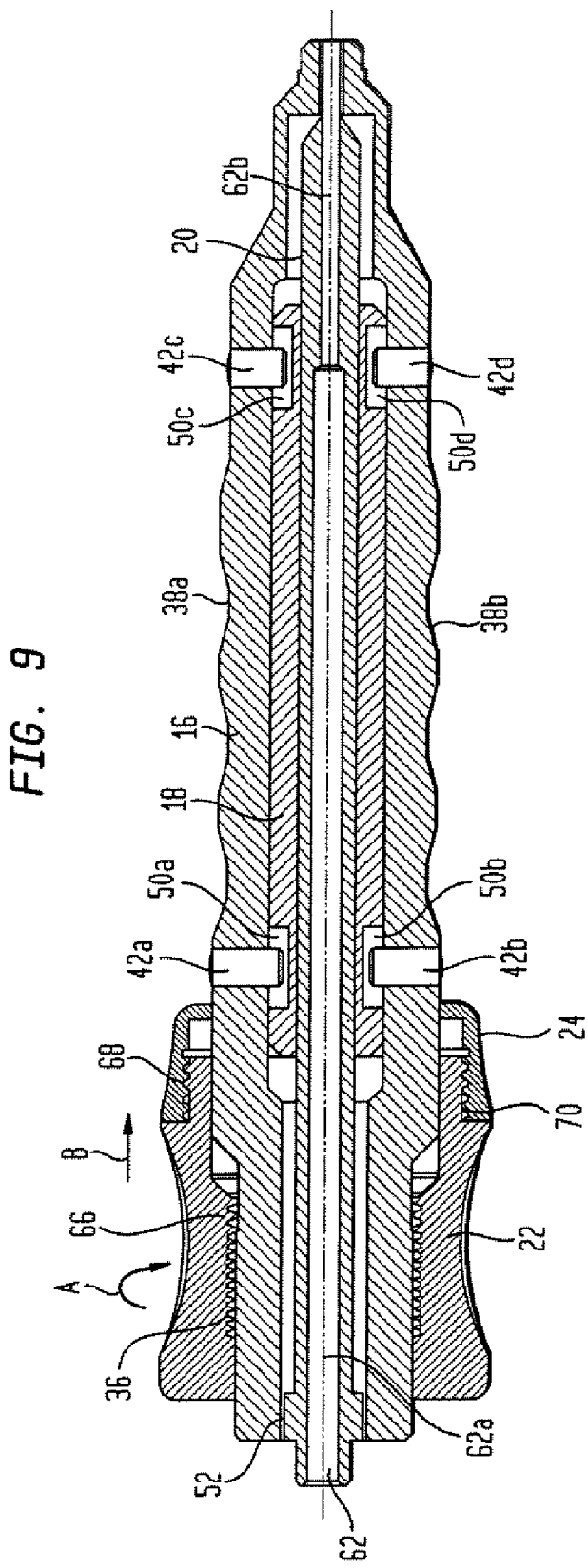
FIG. 9 is a cross sectional side view of the compression instrument shown in FIG. 1.

Referring to FIG. 4, handle 16 is more particularly depicted apart from the other elements of compression instrument 10. As shown in that Figure, as well as in those figures which depict a fully constructed compression instrument 10, handle 16 may provide the majority of the structure included in instrument 10, as well as its elongate nature. In fact, handle 16 essentially extends between the aforementioned proximal and distal ends 12 and 14, and as such, these ends are shown in FIG. 4. Handle 16 is preferably a tubular structure and may include three distinct sections, a distal section 30, a gripping section 32, and a tip section 34. Distal section 30 preferably has a threaded portion 36 for cooperating with knob 22 (this cooperation is best shown in FIG. 9) and a rectangular opening 37 for capturing a portion of sleeve 20 (this cooperation is, best shown in FIGS. 10a and 10b). Additionally, a first part 28a of a channel 28 extends through distal section 30. Gripping section 32 is essentially a larger and/or raised section, with respect to sections 30 and 34. In a preferred embodiment, gripping section 32 may include opposed undulating surfaces 38a and 38b for improved gripping, and a cut out section 40 with protrusions 42a, 42b, 42c and 42d extending therein, for receiving and cooperating with sledge 18. Finally, tip section 34 is preferably circular in cross section, and may include a proximal-most tip 44 for engaging a like sized hole on a plate. In addition, the tip section 34 includes a third part 28c of channel 28 extending therethrough.

Figure 5:
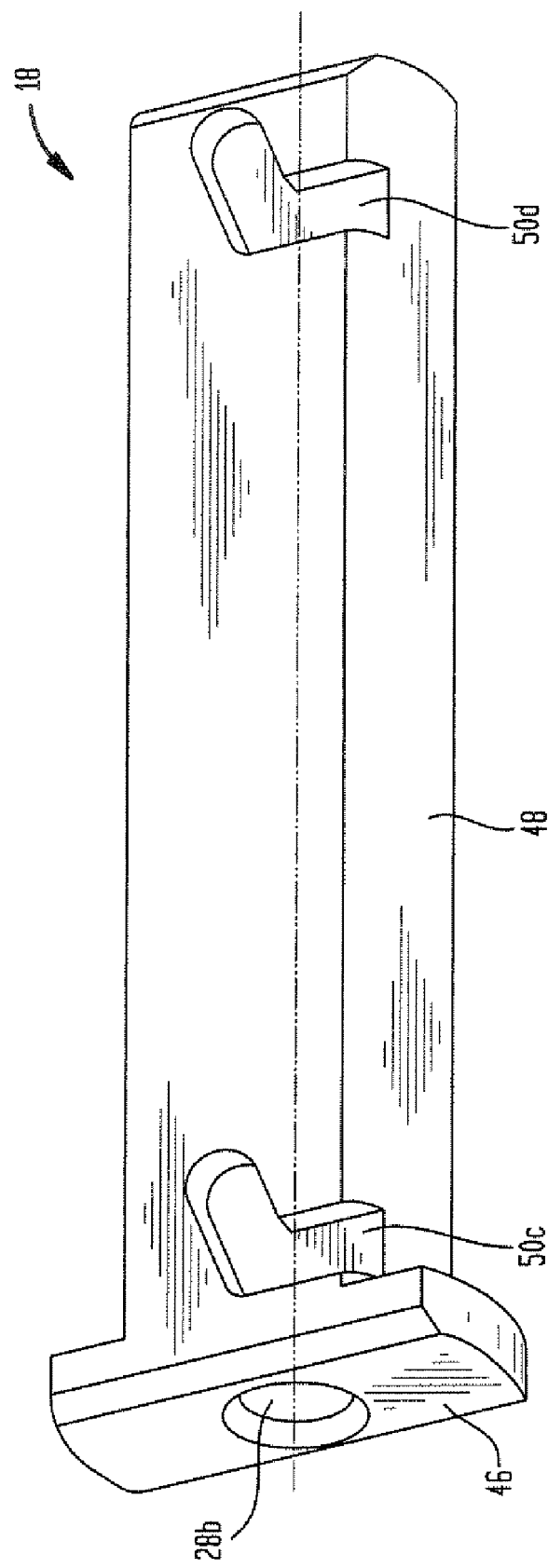
FIG. 5 is a perspective view of a sledge portion of the compression instrument shown in FIG. 1.

As shown in FIG. 5, sledge portion 18 is preferably a unitary body having a first body portion 46 and a second body portion 48, wherein each of the first and second body portions may have a substantially rectangular cross-sectional shape. Additionally, first body 46 is preferably wider than second body 48, so that a portion of it extends beyond the remainder of sledge 18 along at least one direction. This width or size difference allows for cooperation with the other elements of instrument 10 during operation, as will be more fully discussed below. Second body 48 preferably includes four grooves or slots 50a, 50b, 50c and 50d, which may be angled and/or include angled sections that are adapted to mate with protrusions 42a, 42b, 42c and 42d of handle 16. Finally, sledge portion 18 may include a second part 28b of channel 28 extending therethrough.

Thus, channel 28 includes first part or section 28a formed through distal section 30 of handle 16, second part of section 28b formed through sledge 18, and third part or section 28c formed through tip section 34 of handle 16. As a result, a continuous channel 28 may be formed in the fully assembled instrument 10.

Figure 6:
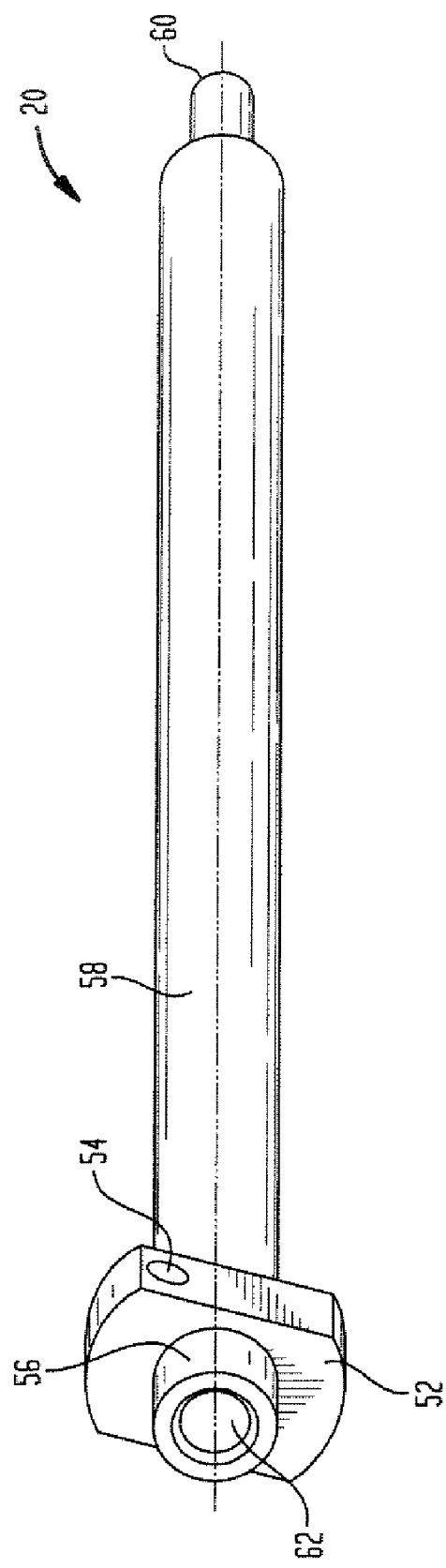
FIG. 6 is a perspective view of a sleeve portion of the compression instrument shown in FIG. 1.

FIG. 6 depicts sleeve 20, which is preferably adapted to fit over a K-wire or other elongate element which, in turn, may be adapted to be embedded in a bony body or the like. Sleeve 20 is also preferably a unitary substantially tubular body sized and configured to fit within channel 28 formed in handle 16 and sledge portion 18. Furthermore, sleeve 20 may be sized and configured to fit within channel 28, such that there may be a predetermined amount of clearance between the sleeve and the first and third parts 28a and 28c, but substantially no clearance between the sleeve and the second part 28b. Thus, sleeve 20 may be sized so as to have a diameter which is somewhat smaller than that of the first and third parts of channel 28, and substantially the same as that of part 28b.

As shown in FIG. 6, sleeve 20 may include a shoulder portion 52 for insertion into the above discussed rectangular opening 37 of handle 16. The rectangular opening 37 may be sized so as to be larger than shoulder portion 52, so as to provide the same or a different amount of clearance there between as compared to the clearance between sleeve 20 and parts 28a and 28c of channel 28. It is noted that the aforementioned spring assembly 26 may be inserted into an opening 54 on shoulder portion 52 so as to prevent sleeve 20 from falling out of a fully constructed instrument 10. In operation, spring assembly 26 may exert a force upon a portion of rectangular opening 37 to prevent the inadvertent movement or removal of sleeve 20 therefrom. The remainder of sleeve 20 may include like sized tubular portions 56 and 58, and a smaller diameter, stepped down tubular portion 60. A sleeve channel 62 (best shown in the cross sectional view of FIG. 9) runs through sleeve 20. As shown in FIG. 9, this channel may include differently sized sections 62a and 62b, or alternatively, may be one size. In a preferred embodiment, sleeve channel 62 is sized to fit a K-wire or the like therein. However, channel 62 may also be sized so as to allow insertion of a rod, nail, screw or the like therein.

Figure 7:
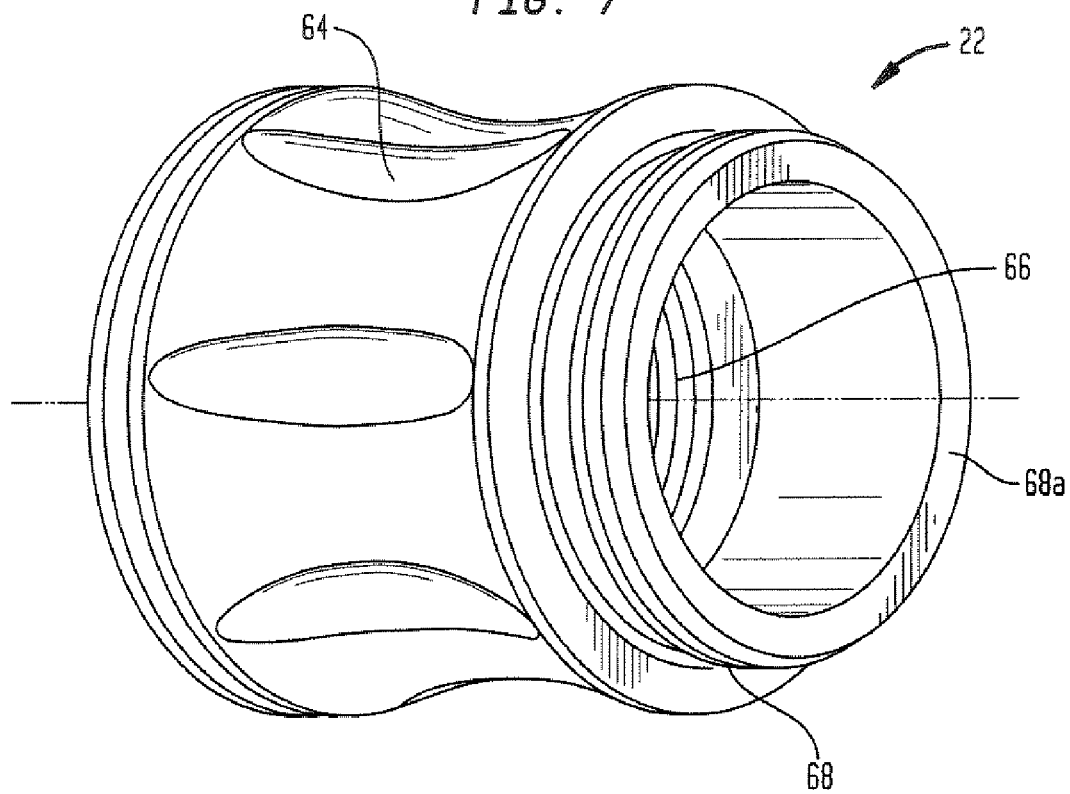
FIG. 7 is a perspective view of a knob portion of the compression instrument shown in FIG. 1.
Figure 8:
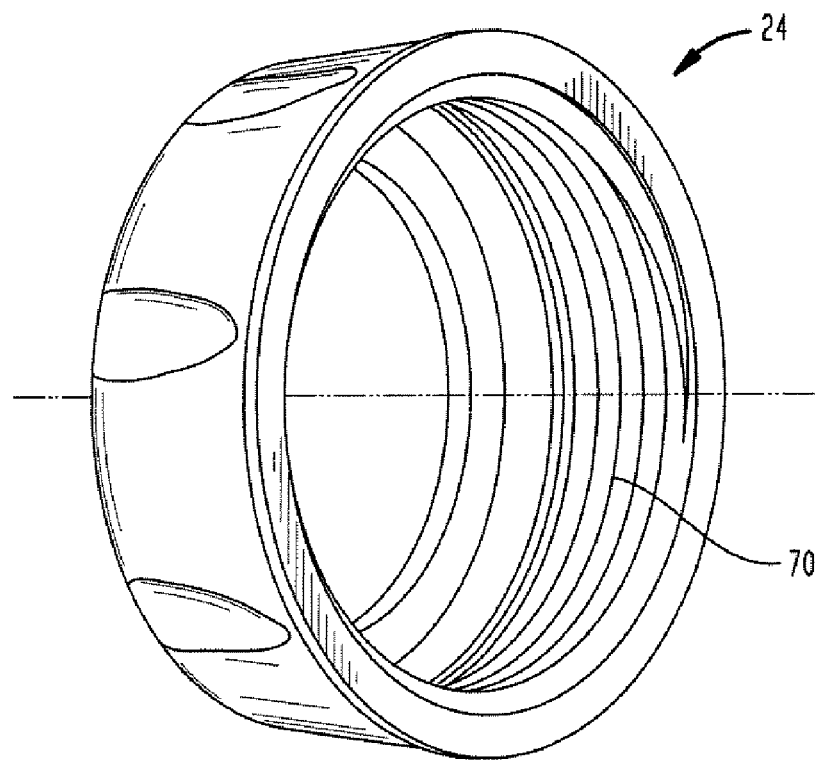
FIG. 8 is a perspective view of a nut portion of the compression instrument shown in FIG. 1.

FIGS. 7 and 8 more specifically depict knob 22 and nut 24, respectively. Knob 22 may be a tubular structure having a gripping surface 64 for allowing easy gripping and rotating by a surgeon or operator. Knob 22 is preferably sized and configured to fit over distal section 30 of handle 16. More specifically, knob 22 may include an internal threaded surface 66 for engaging threaded surface 36 of handle 16. Additionally, knob 22 may also include an external threaded surface 68 for engaging nut 24. Nut 24 may be a tubular structure with an internal threaded surface 70 for engaging the aforementioned external threaded surface 68 of knob 22. Essentially, nut 24 allows the easy assembly and disassembly of instrument 10.

It is noted that the above elements of instrument 10 may vary in their particular construction, including in their size and configuration. For example, sleeve 20 may be sized differently in order to slide over different elongate elements inserted into the bone. In addition, it is noted that the various elements of instrument 10 may be constructed of many different types of materials. For example, the components of instrument 10 may be constructed of bio-compatible materials suitable for insertion into the body of a patient, such as stainless steel or polymer materials. Titanium, aluminum and fiber-reinforced plastics may also be utilized. However, it is also noted that certain elements may be constructed of one type of certain material, while other elements may be constructed from a second and different type of material. For example, handle 16 may be constructed of a polymeric material for easy manufacturing, while sleeve 20 may be constructed of stainless steel to insure acceptable use with stainless steel elongate elements inserted in the bone.

A method of assembly of compression instrument 10 will now be described. However, it is to be understood that different methods of assembly may be undertaken, including assembling of parts in different orders, in different fashions, etc. Initially, sledge 18 may be inserted into cut out section 40 of handle 16, such that protrusions 42a, 42b, 42c and 42d extend into grooves 50a, 50b, 50c and 50d. Thereafter, sleeve 20 may be slid into and through all three parts 28a, 28b and 28c of channel 28, and shoulder portion 52 of sleeve 20 may be inserted into rectangular opening 37 of handle 16. As mentioned above, spring assembly 26 may also be engaged with rectangular opening 37, so as to prevent the inadvertent removal or movement of sleeve 20 from handle 16. As such, sleeve 20 is held in place. Next, knob 22 may be slid over distal section 30 of handle 16, and its internal threaded surface 66 can be threadably engaged with external threaded portion 36 of distal section 30. Once knob 22 is properly arranged on handle 16, it is noted that an end face 68a of surface 68 of knob 22 may abut rectangular body 46 of sledge 18. Thus, any translational motion of knob 22, in a direction depicted by arrow B (FIGS. 9-10b), may be imparted to sledge 18. Finally, nut 24 is slid over tip section 34 and gripping section 32 of handle 16, and threadably engaged with knob 22. That is, internal threaded surface 70 of nut 24 may engage external threaded surface 68 of knob 22. In addition, rectangular body 46 of sledge 18 may be clamped between end face 68a of knob 22 and nut 24, so that translational motion of knob 22 and nut 24 in a direction opposite to that depicted by arrow B (FIGS. 9-10b) will move sledge 18 in the same direction. It should be noted that nut 24 may not contact any other component or portion of any other component of instrument 10. Therefore, knob 22 may be free to rotate and translate or move at least partially along handle 16. This operation will be discussed more fully below. Nonetheless, with nut 24 in position, the various components of instrument 10 may be essentially locked into their assembled position. The final interconnection or assembly of the elements of compression instrument 10 is clearly shown in the cross sectional view of FIG. 9 and in the partial cross sectional views of FIGS. 10a and 10b.

Figure 10A:
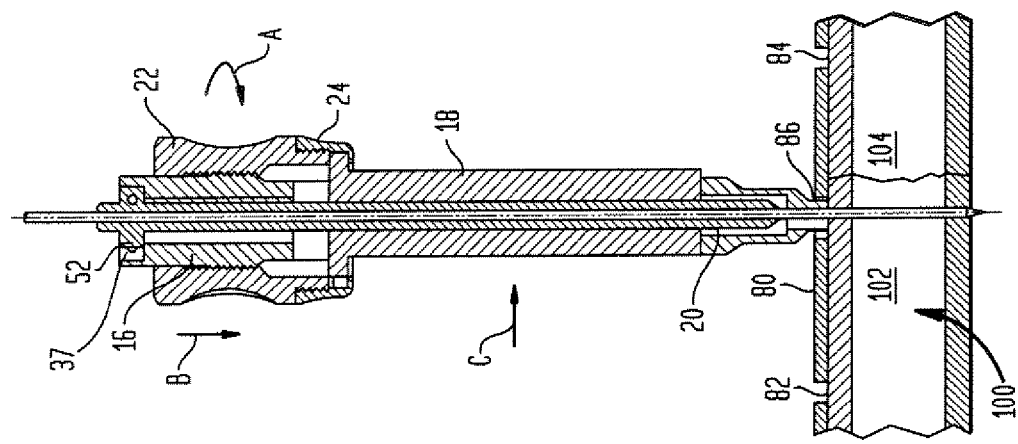
FIGS. 10a and 10b are illustrations depicting use of the compression instrument shown in FIG. 1.
Figure 10B:
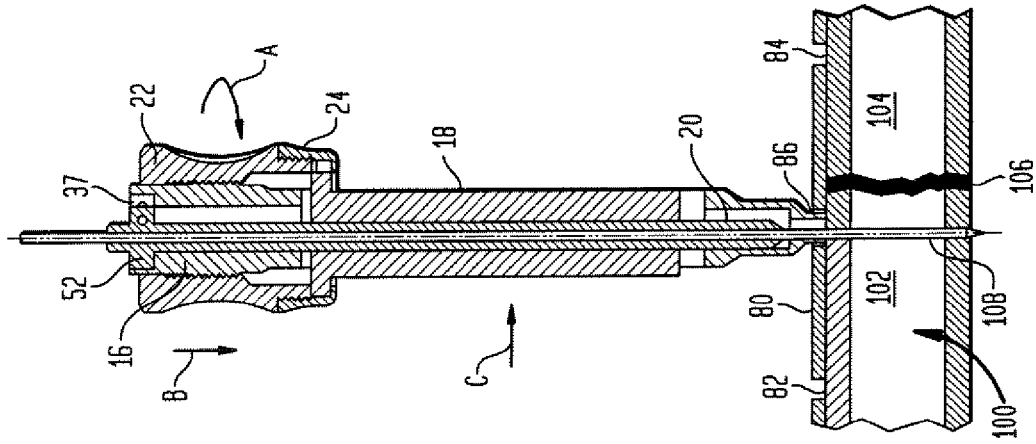

In operation, clockwise rotation of knob 22 (depicted by arrow A in FIGS. 9-10b) causes movement along the longitudinal axis of instrument 10 in a direction depicted by arrow B (FIGS. 9-10b) of both knob 22 and nut 24. As a portion of knob 22 abuts a portion of sledge 18, this longitudinal movement of knob 22 may cause similar longitudinal movement of sledge 18, and may also cause angled grooves 50a, 50b, 50c, and 50d to ride along protrusions 42a, 42b, 42c, and 42d, thereby resulting in translational movement of sledge 18 from one side of open cut out section 40 to the other. In the figures, this translational movement is best described as into and out of the paper in FIG. 9, and between left and right as shown in FIGS. 10a and 10b (denoted by arrow C in FIGS. 10a and 10b). Since sleeve 20 may be tightly disposed within channel part 28b of sledge 18, and free to move somewhat within channel parts 28a and 28c, sleeve 20 may move along with sledge 18. Thus, rotational movement of knob 22 ultimately may cause translational movement of sleeve 20, as well as any elongate structure contained within sleeve channel 62. This will be further described below.

In a surgical procedure, the aforementioned transformation of rotational movement to translational movement, provided by compression instrument 10 is utilized to aid a surgeon in resetting or compressing a bone fracture. As mentioned above, compression instrument 10 may be utilized with many different bone plates or other type of devices, including bone plate 80 depicted in FIGS. 10a and 10b. In the embodiment shown in FIGS. 10a and 10b, bone plate 80 includes at least two screw holes 82 and 84 for allowing mounting to a bone 100, as well as a hole 86 for allowing insertion of tip 44 of compression instrument 10 therein. It is noted that these holes may be similarly sized, or may have different sizes or diameters. For example, certain embodiment bone plates may have oblong holes, slots, threaded holes (e.g. for monoaxial screws), or the like. In addition, it is noted that an attachment outside of the plate is another possibility. As shown in FIG. 10a, bone plate 80 may be placed through an incision in the skin of the patient and onto bone 100 such that it spans across bone fragments 102 and 104 caused by fracture 106. Thereafter, a first screw or other type of fastener means may be inserted into hole 84 such that only that side of bone plate 80 is fixed to bone 100. As a result, only fragment 102 may move relative to plate 80.

Once one side of bone plate 80 is affixed to bone 100 as described above, tip 44 of compression instrument 10 may be inserted through the incision and into hole 86. Upon or prior to such insertion, knob 22 may be turned as far as possible in a counter-clockwise direction. As such, sledge 18 may be disposed as far to one side as possible. Additionally, instrument 10 may be orientated or positioned within hole 86 such that sledge 18 is set as far away from fracture 106 as possible, so that any movement of sledge 18 would compress or close the fracture, as illustrated in FIGS. 10a and 10b. With instrument 10 in this position, a K-wire 108 or the like may be inserted through the cannulated components of the instrument 10 and into fragment 102 of bone 100, as shown in FIG. 10a. As shown therein, such position of instrument 10, and more particularly sledge 18 and sleeve 20, causes K-wire 108 to be situated to one side of hole 86 (which is the side of hole 86 further away from fracture 106). The K-wire 108 may be inserted bicortical.

After instrument 10 has been inserted into hole 86 of bone plate 80 and K-wire 108 has been inserted through instrument 10 and into bone fragment 102, as previously described, the next step in the surgical procedure, that is, the rotation of knob 22 may be performed. It is noted that handle 16 may be held during this rotation such that the orientation of instrument 10, as shown in FIGS. 10a and 10b, is retained. As discussed above, rotation of knob 22 may cause translational movement of sledge 18 and sleeve 20. Therefore, performing the knob rotational step may cause these components, as well as K-wire 108, to be shifted to the position depicted in FIG. 10b. As a result, fragment 102 may also move along with K-wire 108, thereby compressing fracture 106 and returning bone 100 to a pre-fracture state. At this time, a second screw or other type of fastener means may be inserted into hole 82 such that bone plate 80 is fixed to both fragments of bone 100, and fragments 102 and 104 can no longer move with respect to one another. Finally, instrument 10 and K-wire 108 may be removed. The hole formed in bone 100 by K-wire 108 may be bored up and/or another screw may be placed into and through hole 86. As a result of this surgical procedure, fragments 102 and 104 may remain in their final position (FIG. 10*b*) and recalcify to form one solid bone.

It is to be understood that the above described surgical procedure may include additional and/or different steps. For example, instead of inserting K-wire 108 after insertion of instrument 10 into hole 86, the K-wire may be inserted into bone 100 before the instrument 10 is inserted into hole 86. In this example, the instrument 10 may be inserted over the K-wire and into hole 86. As another example, rather than implanting a K-wire 108 into bone 100, other types of elements or structures may be inserted into the bone (e.g., drills, pins, bolts, nails, taps, threaded pins etc.). Clearly, instrument 10 may be sized differently depending upon the bone fixation structure to be utilized. In addition, it is noted that instrument 10 may be utilized to displace fragments, as opposed to compressing same. During such use of instrument 10, the surgeon or other medical professional may position instrument 10 and any elongate element (e.g., K-wire 108) so that rotation of knob 22 causes one of the bone fragments to move apart from the other. This may be useful where compression fractures or the like occur in a section of a bone. Therefore, and as would be apparent to those of ordinary skill in the art, the direction of compression/displacement may be adjusted by differently orienting instrument 10 and its various components. While FIGS. 10*a* and 10*b* depict a simple straight fracture of an elongate bone, many fractures are not that simple. For such non-simple fractures, a surgeon or other medical professional may need to move bone fragments in several directions during the bone resetting process. In such circumstances, the orientation of instrument 10 may be changed accordingly.

In addition, a bone plate may be attached to both fragments where compression/displacement is to occur, prior to such compression/displacement. In this situation, a bone plate may be provided having an elongate slot on the side of the fracture line which includes the bone fragment to be moved. The bone plate may be attached to the moveable fragment with a fixation means (such as a screw or other type of fastener) through this slot. As is to be appreciated, such fixation means or screw may not be fully tightened or secured at this time. Thereafter, the instrument 10 would be operated to cause the fragment to move and the fixation means to ride along the slot. Upon the desired positioning being achieved, the fixation means or screw may be tightened to permanently affix the bone plate to the bone. Additionally, another fixation means may be inserted through the plate and into the bone.

Furthermore, it is noted that instrument 10 may be used in conjunction with one or more bone plates to reset a bone with more than one fracture. For example, utilizing the configuration depicted in FIGS. 10*a* and 10*b*, a second fracture may be located on either side of fracture 106. Once the first fracture 106 is reset in accordance with the above described process or the like, instrument 10 may be moved to another hole situated in a position suitable for compressing the second fracture. Afterwards, a surgeon or other medical professional would simply re-perform the above noted steps to compress and fix the second fracture. This procedure may be done over and over again depending upon the overall number or type of fractures. As the particulars of the fractures with respect to one another may vary tremendously, to help accommodate such variation, the bone plate may be adapted or configured to be easily drillable so as to provide a number of holes each of a desired size and at a desired location which would be suitable to perform the above noted steps. Such would be completely understood by those of ordinary skill in the art.

Additionally, instrument 10 may be configured differently from that described above. As an example, sleeve 20 may be omitted and sledge 18 may be modified to accommodate the K-wire. In a further example, it is noted that knob 22 may be designed so that a force different than that of rotation could be applied thereto in order to create the translational movement to sledge 18. In one envisioned embodiment, it may be possible to provide a knob 22, where a downward force to the knob would provide the desired translational movement to sledge 18.

Figure 11:
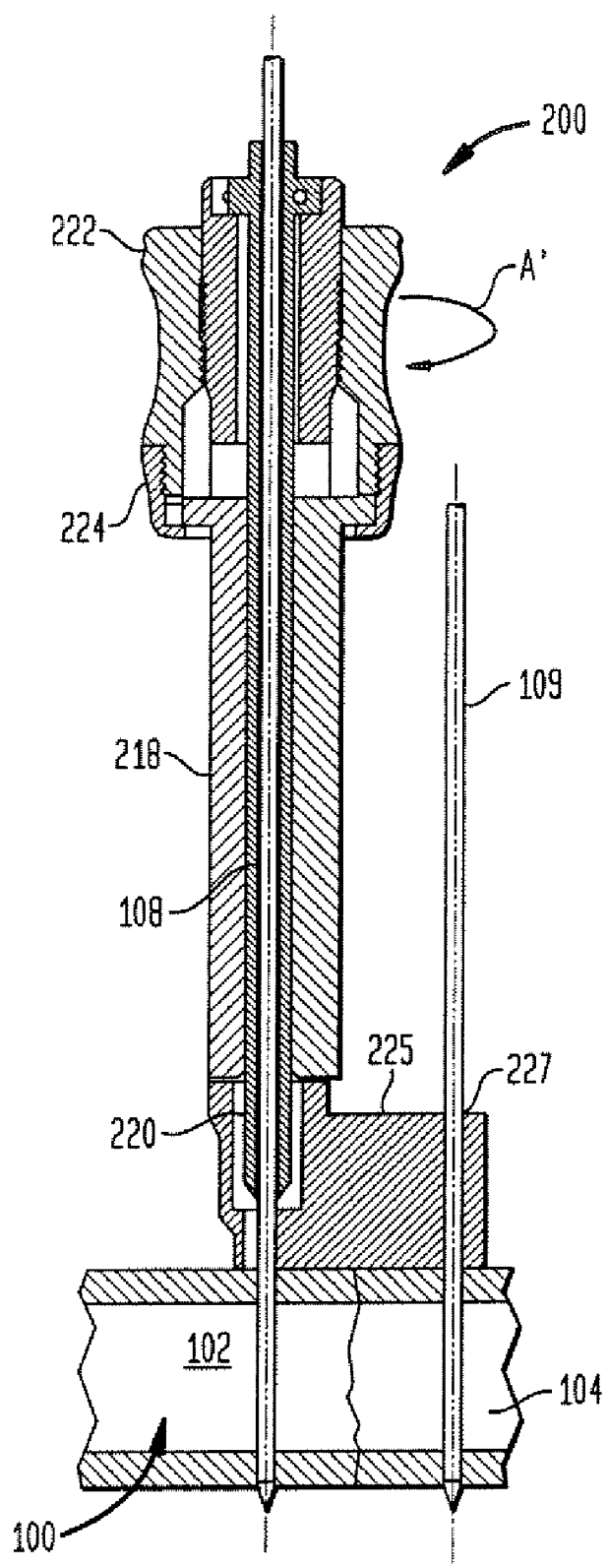
FIG. 11 is an illustration depicting use of a compression instrument according to a second embodiment of the present invention.

Finally, FIG. 11 depicts a second embodiment instrument 200. Like that of the above described instrument 10, instrument 200 may include many like elements, although designated with reference numerals within the 200-series of numbers. For example, instrument 200 may include a handle 216, a sledge portion 218, a K-wire sleeve 220, a knob 222 and a nut 224. It is noted that these elements preferably operate in a similar fashion to that of instrument 10, so that instrument 200 can also perform a similar function. However, rather than cooperating with a bone plate or the like, instrument 200 includes a lateral portion 225 having a hole 227 formed therethrough for engaging a second elongate element. Like that of instrument 10, in operation, clockwise rotation of knob 222 (depicted by arrow A' in FIG. 11) preferably ultimately causes sleeve 220 to move towards or away from lateral portion 225 and hole 227.

In one surgical procedure utilizing instrument 200, rather than utilizing a bone plate or the like, a surgeon may simply place instrument 200 adjacent bone 100, so that sleeve 218 rests over fragment 102 and hole 227 rests over fragment 104. Thereafter, the surgeon may utilize the tubes of sleeve 218 and hole 227 to guide the insertion of K-wires (108 and 109, respectively) into bone fragments 102 and 104. It is noted that other elongate elements, such as those discussed above, may be utilized. In addition, it is noted that such elongate elements may be inserted prior to placing instrument 200 adjacent bone 100. Once both elongate elements 108 and 109 are inserted in bone 100 and instrument 200 is engaged therewith, operation of the instrument, like that operation described in conjunction with instrument 10, should cause fragment 102 to move towards fragment 104. Thus, the same result may be achieved with instrument 200 as that which is achieved with instrument 10, without the use of a bone plate or the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone compression/displacement system comprising:
a bone plate having at least one plate hole;
an elongate member extending through said plate hole; and
an instrument including:
 a handle having a longitudinal axis;
 a sledge arranged in a portion of said handle, said sledge being movable with respect to said handle, said handle and said sledge forming a channel extending therethrough;
 a knob connected to said handle; and
 a sleeve inserted through said handle and said sledge, said sleeve being cannulated for receiving said elongate element therethrough, said sleeve including a shoulder portion disposed within an opening in said handle and a spring assembly associated with the shoulder portion, wherein said elongate member extends through said channel and out of said instrument, and movement of said knob causes movement of said sledge with respect to said handle, the movement of said sledge being in a direction perpendicular to the longitudinal axis of said handle.

2. The bone compression/displacement system of claim 1, wherein said handle includes a cut out section for receiving said sledge and first and third parts of the channel for receiving said sleeve.

3. The bone compression/displacement system of claim 2, wherein said sledge includes a second part of the channel for receiving said sleeve.

4. The bone compression/displacement system of claim 3, wherein said sleeve is sized to move within said first and third parts of said channel.

5. The bone compression/displacement system of claim 1, wherein said knob is threadably connected to said handle.

6. The bone compression/displacement system of claim 5, further comprising a nut threadably connected to said knob.

7. The bone compression/displacement system of claim 1, wherein said sledge includes at least one groove for cooperating with at least one protrusion of said handle.

8. The bone compression/displacement system of claim 7, wherein rotation of said knob causes translation of said sledge in a direction perpendicular to the longitudinal axis of said handle.

9. The bone compression/displacement system of claim 1, wherein said handle further includes a tip for insertion into the at least one bone plate hole.

10. The bone compression/displacement system of claim 1, wherein said sleeve includes two differently sized tubular portions.

11. The bone compression/displacement system of claim 1, wherein said channel extends through said knob.

12. The bone compression/displacement instrument-system of claim 1, wherein said elongate element is a k-wire.

13. A bone compression/displacement system comprising:
a bone plate having at least one plate hole;
an elongate member extending through said plate hole; and
an instrument including:
a handle having a longitudinal axis;
a sledge arranged in a portion of said handle, said sledge being movable with respect to said handle, said handle and said sledge forming a channel extending therethrough, said sledge including at least one groove for cooperating with at least one protrusion of said handle;
a knob connected to said handle; and
a sleeve inserted through said handle and said sledge, said sleeve being cannulated for receiving said elongate element therethrough, said sleeve including a shoulder portion disposed within an opening in said handle and a spring assembly associated with the shoulder portion, wherein said elongate member extends through said channel and out of said instrument, and rotation of said knob causes translation of said sledge with respect to said handle in a direction perpendicular to the longitudinal axis of said handle.

14. The bone compression/displacement system of claim 13, wherein said handle includes a cut out section for receiving said sledge and first and third parts of the channel for receiving said sleeve.

15. The bone compression/displacement system of claim 14, wherein said sledge includes a second part of the channel for receiving said sleeve.

16. The bone compression/displacement system of claim 15, wherein said sleeve is sized to move within said first and third parts of said channel.

17. The bone compression/displacement system of claim 13, wherein said knob is threadably connected to said handle.

18. The bone compression/displacement system of claim 17, further comprising a nut threadably connected to said knob.

19. The bone compression/displacement system of claim 13, wherein said handle further includes a tip for insertion into the at least one bone plate hole.

20. The bone compression/displacement system of claim 13, wherein said sleeve includes two differently sized tubular portions.

21. The bone compression/displacement system of claim 13, wherein said channel extends through said knob.

22. The bone compression/displacement system of claim 13, wherein said elongate element is a k-wire.

* * * * *

UNITED STATES PATENT AND TRADEMARK OFFICE
CERTIFICATE OF CORRECTION

| | | |
|---|---|---|
| PATENT NO. | : 7,704,257 B2 | Page 1 of 1 |
| APPLICATION NO. | : 11/285808 | |
| DATED | : April 27, 2010 | |
| INVENTOR(S) | : Beat Mürner | |

It is certified that error appears in the above-identified patent and that said Letters Patent is hereby corrected as shown below:

Column 9, line 39, change "displacement Instrument-sys" to --displacement sys--.

Signed and Sealed this
Twelfth Day of April, 2011

David J. Kappos
*Director of the United States Patent and Trademark Office*